United States Patent [19]

Ragnarsson et al.

[11] Patent Number: 4,942,040
[45] Date of Patent: Jul. 17, 1990

[54] PHARMACEUTICAL PREPARATION AND A PROCESS FOR ITS PREPARATION

[75] Inventors: Gert A. Ragnarsson, Bro; Kajsa M. Silfverstrand, Gothenburg; John A. Sjögren, Mölnlycke, all of Sweden

[73] Assignee: Aktiebolaget Hassle, Molndal, Sweden

[21] Appl. No.: 250,945

[22] Filed: Sep. 29, 1988

[30] Foreign Application Priority Data

Oct. 8, 1987 [SE] Sweden .................. 8703881

[51] Int. Cl.$^5$ .............................................. A61K 9/26
[52] U.S. Cl. .................. 424/486; 424/459; 424/461; 424/462; 424/470; 424/487; 424/488; 424/469
[58] Field of Search .............. 424/489, 490, 468, 470, 424/486, 469, 461, 462, 487, 488

[56] References Cited

U.S. PATENT DOCUMENTS

| | | | |
|---|---|---|---|
| 3,726,897 | 4/1973 | Schindler et al. | 514/963 X |
| 3,870,790 | 3/1975 | Lowey et al. | 424/19 |
| 3,951,821 | 4/1976 | Davidson | 252/1 |
| 4,016,880 | 4/1977 | Theeuwes et al. | |
| 4,083,949 | 4/1978 | Benedikt | 424/19 |
| 4,123,382 | 10/1978 | Morse et al. | 514/963 X |
| 4,169,069 | 9/1979 | Unger et al. | 514/963 X |
| 4,193,985 | 3/1980 | Bechgaard et al. | 424/458 X |
| 4,226,849 | 10/1980 | Schor | 424/480 X |
| 4,256,108 | 3/1981 | Theeunes | 424/473 |
| 4,259,314 | 3/1981 | Lowey | 424/480 X |
| 4,291,016 | 9/1981 | Nougaret | 424/480 X |
| 4,309,404 | 1/1982 | DeNeale et al. | 424/489 |
| 4,309,406 | 1/1982 | Guley et al. | 424/489 |
| 4,326,525 | 4/1982 | Swanson et al. | 424/473 |
| 4,341,759 | 7/1982 | Bogentoft et al. | 424/458 X |
| 4,357,469 | 11/1982 | Schor | 424/480 X |
| 4,369,272 | 1/1983 | Schor et al. | 424/480 X |
| 4,404,183 | 9/1983 | Kawata et al. | 424/480 X |
| 4,415,547 | 11/1983 | Yu et al. | 424/19 |
| 4,434,153 | 2/1984 | Urquhart et al. | 424/469 |

(List continued on next page.)

FOREIGN PATENT DOCUMENTS

| | | |
|---|---|---|
| 1180277 | 1/1985 | Canada . |
| 0013263 | 7/1980 | European Pat. Off. . |
| 0061217 | 9/1982 | European Pat. Off. . |
| 0068324 | 1/1983 | European Pat. Off. . |
| 0123470 | 10/1984 | European Pat. Off. . |
| 0148811 | 7/1985 | European Pat. Off. . |
| 0163984 | 12/1985 | European Pat. Off. . |
| 0220143 | 4/1987 | European Pat. Off. . |
| 2030501 | 12/1971 | Fed. Rep. of Germany . |
| 58-170712 | 10/1983 | Japan . |
| 1542414 | 3/1979 | United Kingdom . |
| 2098867 | 12/1982 | United Kingdom . |
| 2154874 | 9/1985 | United Kingdom . |
| 2159715 | 12/1985 | United Kingdom . |
| WO82/03009 | 9/1982 | World Int. Prop. O. . |
| WO85/03436 | 8/1985 | World Int. Prop. O. . |

OTHER PUBLICATIONS

"Controlled Release From Dosage Forms", Bogentoft, C., and Sjogren, J., Dept. of Pharmaceutics, Hassle, Sweden, 1980.
Elsevier/North-Holland Biomedical Press, Towards Better Safety Safety of Drugs and Pharmaceutical Products, pp. 229–246.
Abstract of European Patent Appln. 0 068 324.
British Journal of Clinical Pharmacology, Supplement 2 to vol. 19, 1985, pp. 69S–224S, "Osmotic Delivery Systems for the Beta-Adrenoceptor Antagonists Metoprolol and Oxeprenolol: Design and Evaluation of Systems for Once-Daily Administration", F. Theeuwes, D. R. Swanson, G. Guittard, A. Ayer & S. Khanna.
Pharmaceuticals–pp. 10–11, vol. 86, No. 37, J8 6040647-B.

(List continued on next page.)

Primary Examiner—Thurman K. Page
Attorney, Agent, or Firm—White & Case

[57] ABSTRACT

Preparation giving a controlled and extended release of both a dihydropyridine, e.g. felodipine and a β-adrenoreceptor antagonist, namely metoprolol as well as a method for the manufacture of the new preparation.

11 Claims, 2 Drawing Sheets

—△— Example 1, fixed extended-release combination
—○— Reference example A, felodipine conventional tablet

U.S. PATENT DOCUMENTS

| | | | |
|---|---|---|---|
| 4,439,195 | 3/1984 | Swanson et al. | 424/473 |
| 4,449,983 | 5/1984 | Cortese et al. | 424/434 |
| 4,484,921 | 11/1984 | Swanson et al. | 424/473 |
| 4,510,150 | 4/1985 | Berthold | 514/338 |
| 4,537,898 | 8/1985 | Hoff et al. | 424/480 X |
| 4,558,058 | 12/1985 | Schonafinger et al. | 514/342 |
| 4,578,075 | 3/1986 | Urquhart et al. | 424/453 |
| 4,587,267 | 5/1986 | Drake et al. | 514/769 |
| 4,642,233 | 2/1987 | Urquhart et al. | 424/486 |
| 4,649,043 | 3/1987 | Urquhart et al. | 424/486 |
| 4,681,583 | 7/1987 | Urquhart et al. | 424/467 |
| 4,681,755 | 7/1987 | Colombo et al. | 424/486 |
| 4,780,318 | 10/1988 | Appelgren et al. | 424/469 |
| 4,794,111 | 12/1988 | Posanski et al. | 514/344 X |
| 4,808,413 | 2/1989 | Joshi et al. | 424/458 |

OTHER PUBLICATIONS

European Journal of Clinical Pharmacology (1982), 21:389–390.

European Journal of Clinical Pharmacology (1983), 24:1–5.

Drugs 29 (Suppl. 2): 131–136 (1985).

Int. J. Pharm. Tech. & Prod. Mfg., 5(3), 1–9, 1984.

International Journal of Pharmaceutics, 2 (1979), 307–315.

Techniques of Solubilization of Drugs (1981), Marcel Dekker, Inc., Edited by Samuel H. Yalkowsky, The Upjohn Co., Kalamazoo, Mich., Clinical Pharmacology and Therapeutics, vol. 22, No. 2, Aug. 1977, pp. 125–130.

Am. J. Cardiol., 1986 Apr., 1:57 (10):733–737.

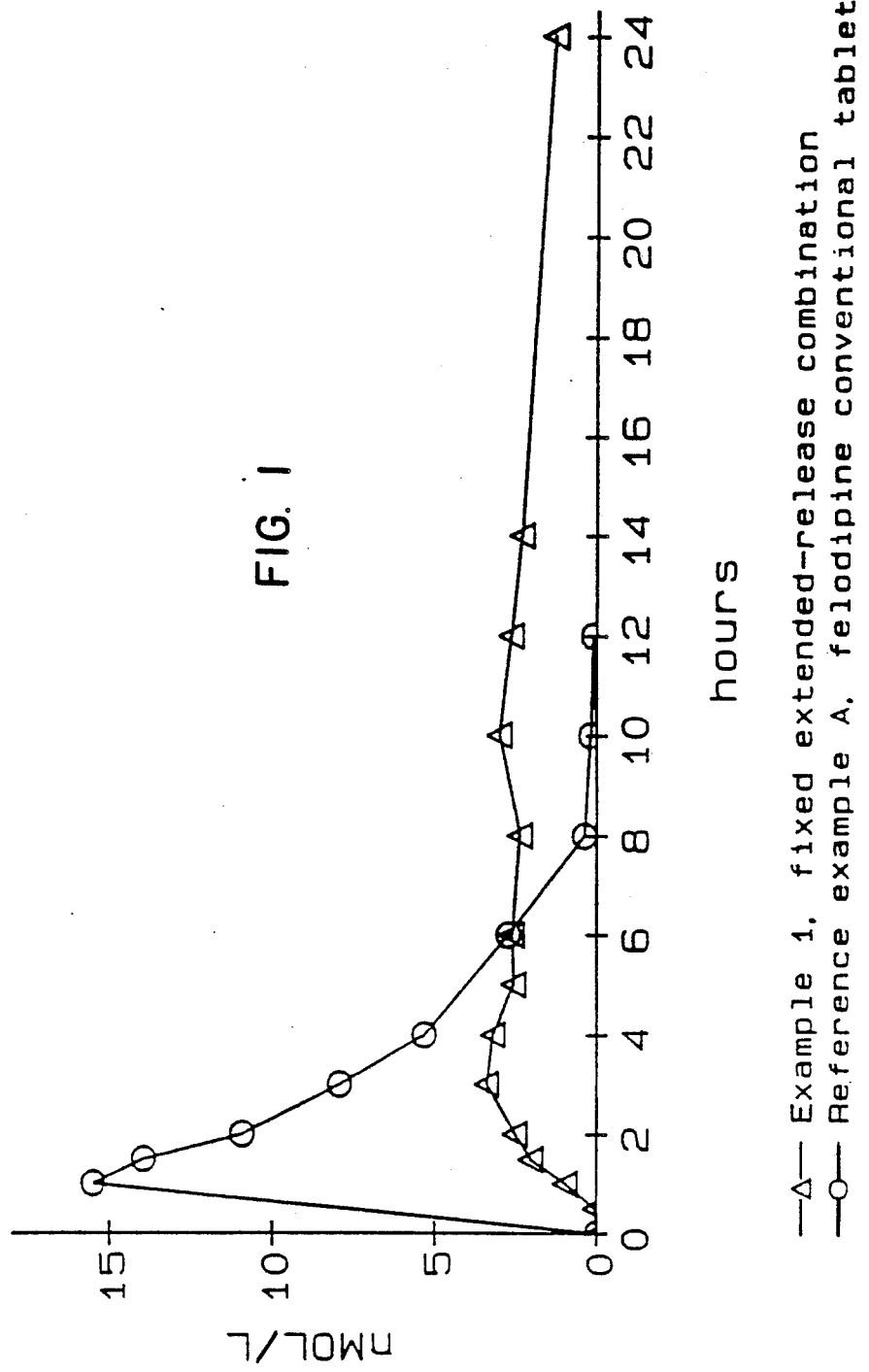

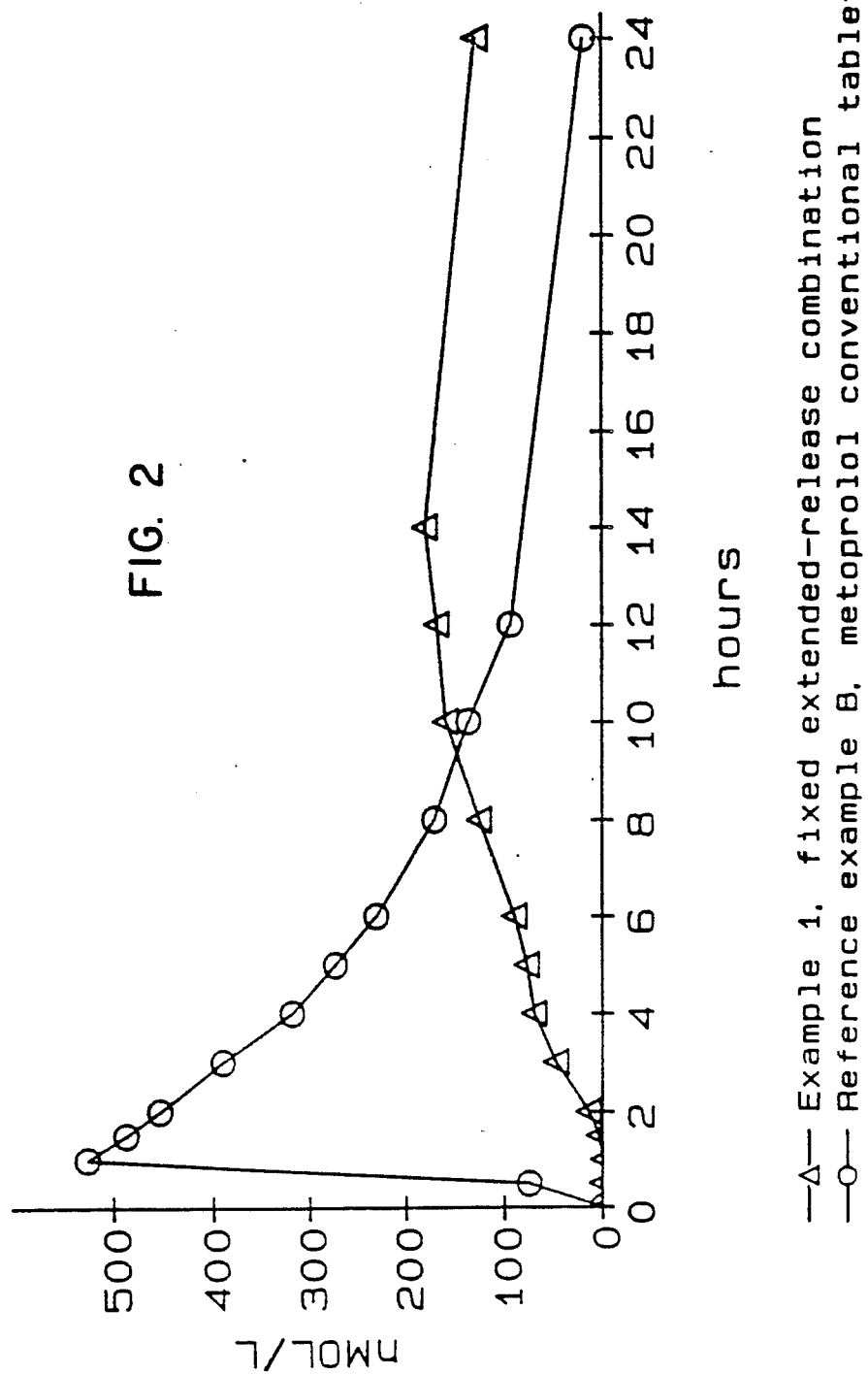

PHARMACEUTICAL PREPARATION AND A PROCESS FOR ITS PREPARATION

FILED OF THE INVENTION

The present invention is related to pharmaceutical extended-release preparations of two drugs of which one is a poorly water soluble compound, namely a calcium channel blocking agent of the dihydropyridine type, and the other is a salt of the β-adrenoreceptor antagonist metoprolol, and to methods of preparing such preparations.

The object of this invention is to obtain a solid preparation with a high extent of bioavailability of the two drugs in combination with an extended absorption from the gastrointestinal tract thus acheiving an even effect over 24 hours after once daily administration.

BACKGROUND OF THE INVENTION

The pharmacological agents calcium antagonists of the dihydropyridine type and β-adrenoreceptor antagonists are widely used in the treatment of cardiovascular disorders.

The mentioned dihydropyridines, e.g. felodipine, nifedipine and nitrendipine, are commonly used in the treatment of cardiovascular disorders like arterial hypertension and ischemic heart disease. The dihydropyridines reduce vascular resistance and load of the heart through a direct effect on the smooth muscles of the blood vessels. The dihydropyridines are characterized by an extremely low solubility in water and for such drugs a low and variable extent of absorption is often seen as the dissolution of the drug in vivo may be rate-limiting.

Several ways to increase drug absorption have been described in the prior litterature. One way is described in No. DE-A-3024858, where a sparingly soluble substituted dihydropyridine, nicardipine, is used in its amorphous form in order to obtain increased absorption of the active compound from the intestine. Another way is described in No. EP-A-47899, where very small crystals of a practically insoluble dihydropyridine, nifedipine, have been used in order to increase the extent of the bioavailability. These methods and others are also described in "Techniques of solubilization of drugs", Ed S. H. Yalkowsky in Drugs and the pharmaceutical sciences, Vol 12. Of particular relevance to the present invention is that surfactant solubilizing agents may be employed in order to increase the bioavailability of the drugs with very low solubility. It is stated that the improvement of absorption properties can be ascribed to three processes: (1) increased wetting (2) increased permeability of membranes and (3) solubilization.

In vivo, the plasma concentration versus time profile after administration of dihydropyridine conventional tablets is characterized by high peak concentrations and comparatively low trough levels. The blood pressure response mirrors the plasma concentration curve, i.e. there is a pronounced effect at the time of the peak and a much less effect after 24 hours. Accordingly, a conventional tablet is not optimal for once daily administration and the more even plasma concentrations produced by a controlled release preparation of high quality would be preferred.

Conventionally, controlled and extended release is achieved by controlling dissolution and/or diffusion of medicament from the dosage form. Several materials are employed for this purpose e.g waxes, fatty materials, polymers, natural, synthetic and semisynthetic gums. Among the gums, hydroxypropyl methylcellulose (HPMC) constitutes an important class because of its pH-independent properties as well as its semisynthetic origin. A review of cellulose ethers in hydrophilic matrices for oral controlled release dosage forms is given by Alderman D.A. Int.J.Pharm. Tech. & Prod. Mfr (1984), 5(3) 1–9. The chemical treatment of HPMC to generate a desired constitution and the use of these qualities are disclosed in U.S. Pat. Nos. 3,870,790, 4,226,849, 4,357,469 and 4,369,172. SE-A-8008646-5 describes a combination of HPMC and hydroxypropyl cellulose which is used to control the release rate of a pharmaceutically active compound.

When a hydrophilic matrix is used the soluble polymer forms a gelatinous layer around the tablet after exposure to gastro-intestinal fluids or saliva. The release of the drug is limited by the rate of water penetration into, and diffusion of drug through, the gel formed (Bamba et al. Int.J.Pharm. (1979),2,307). Erosion of the gel structure is also an important release mechanism of a drug from the system. The polymers used have to hydrate rapidly in order to protect the tablet from fast dissintegration (Alderman 1984).

Drugs with a very low solubility in water may be poorly absorbed from the gastro-intestinal tract due to incomplete or slow dissolution. Consequently it is difficult to increase the duration of effect through a controlled slow dissolution of such a drug without lowering the bioavailability (Bogentoft C and Sjögren J, Towards Better Safety of Drugs and Pharmaceutical Products, Editor D.D. Breimer, 1980 Elsevier/North Holland Biomedical Press).

The β-adrenoreceptor antagonists block the adrenergic stimulation of the heart and thus reduce the oxygen demand of the cardiac tissue. Apparently, this explains their beneficial effects in angina pectoris and cardioprotective action in myocardial infarction. In addition, β-adrenoreceptor antagonists normalize blood pressure in a large proportion of patients with arterial hypertension which probably is due to an additional action on the control of peripheral resistance to blood-flow. For patients treated with β-adrenoreceptor antagonists for cardiovascular disorders it is advantageous to have a constant concentration of the administered drug in the blood. For dosage once a day the β-adrenoreceptor antagonist metoprolol has been incorporated in controlled release tablets of the insoluble matrix type, e.g. Durules ®. However, the drug release from the matrix tablets is not satisfying as about 50 % of the dose is released within a few hours after administration. For a drug like metoprolol with a comparatively short half-life a slower release rate is required in order to obtain even plasma concentrations over 24 hours. A constant release of metoprolol over 20–24 hours would be preferred. A preparation of metoprolol with such properties is described in No. EP-A-220 143.

It has been shown that a combination of a β-adrenoreceptor antagonist and a vasodilating dihydropyridine is of advantage in many hypertensive patients since the two agents have synergistic effects (Hansson BG et al, Drugs 1985:29 (suppl 2); 131–135, Eggerston R and Hansson L Eur. J. Clin. Pharmacol 1982:21;389–390). In addition to the synergistic effects, a co-administration offers advantages regarding decrease in unwanted reflex counteractions elicited by either drug when administered alone (Dean S. and Kendall M. J. Eur. J. Clin. Pharmacol 1983:24;1–5).

Immediate release solid dosage forms of the fixed combination of a dihydropyridine derivative and a β-adrenoreceptor antagonist with improved bioavailability are described in No. EP-A-163984.

However, a fixed combination of the two drugs in a preparation producing reproducible and even plasma concentrations of both drugs over the dosage interval after once daily administration has not been available. The large difference in physical-chemical properties between the two drugs makes it extremely difficult to obtain a suitable preparation based on conventional controlled release systems. A controlled release preparation of the two drugs would improve therapy through less frequent administration and improved patient compliance, (cf Hayes R. B. et al. Clin.Pharm. Ther (1977), 22, p. 125–130) may be obtained with controlled-release dosage forms. Although there has been a need for a controlled release preparation, expressed as far back as in 1977, for a once daily administration of the two drugs, such a preparation has not been available until the present inventors developed the preparation described in the following text.

BRIEF DESCRIPTION OF THE DRAWINGS

FIGS. 1 and 2 shows the means plasma curves as well the average concentrations in plasma after administration of single doses for felodipine and metoprolol respectively.

DESCRIPTION OF THE INVENTION

It is the object of the present invention to provide a preparation giving a high and reproducible extent of absorption as well as even plasma concentration during 24 hours after once daily administration of both a poorly water soluble calcium channel blocking agent of the dihydropyridine type, e.g. felodipine or nifedipine and a β-adrenoreceptor antagonist, namely a salt of metoprolol. As a conventional controlled release preparation cannot give the desired release properties of the two drugs simultaneously it has been necessary to develop a new type of controlled release preparation, which utilises more than one mechanism for controlling the release of the active ingredients. The two drugs are because of that incorporated into one product utilizing two separate mechanisms for controlling the release of the two active ingredients, namely one for the dihydropyridine part and one for the β-adrenoreceptor antagonist part.

The dihydropyridine compounds suitable for the controlled release preparations according to the invention are poorly soluble dihydropyridine compounds. The invention is especially advantageous for compounds with a solubility of less than 0.1 per cent by weight in water and which are solubilizable in a solubilizer of choice or in a combination of a solubilizer and water. Examples of drugs suitable according to the invention are some substituted dihydropyridines, such as nifedipine and felodipine. Felodipine is 4-(2,3-dichlorophenyl)-1,4-dihydro-2,6-dimethyl-3,5-pyridinedicarboxylic acid ethyl methyl ester. Nifedipine is 1,4-dihydro-2,6-dimethyl-4-(2-nitrophenyl)-3,5-pyridinecarboxylic acid dimethyl ester. Other examples are nimodipine, nisoldipine and nitrendipine.

The dihydropyridine is mixed with a hydrophilic swelling agent, e.g. hydroxypropyl methylcellulose (HPMC). From this mixture solid dosage forms such as tablets or capsules are prepared. When such a preparation comes in contact with water it forms a swollen gel matrix, out of which the drug is slowly released.

Among different hydrophilic materials tested, HPMC is a suitable gel-forming material. Other suitable examples of hydrophilic substances are guar gum, xanthan gum, carboxymethylen and different cellulosic materials e.g. sodium carboxymethylcellulose and hydroxypropyl cellulose.

It is preferable to mainly use HPMC having a hydroxypropoxy content of 4–12 weight-%, especially about 8.5 weight-% and a viscosity lower than 100 cps. HPMC of higher viscosity may be added to achieve the optimal rate of drug release. The viscosity is measured by a standardized method described e.g in United States Pharmacopoeia XXI, 1985, p. 672.

The dihydropyridine is preferably dispersed in a nonionic solubilizer before incorporation into the matrix. The solubilizer permits dilution with water or intestinal fluids without the dihydropyridine being transformed into a poorly absorbable form. The choice of solubilizer is critical. With some commonly used solubilizers or co-solvents dilution may cause precipitation of the drug. The mixture of the dihydropyridine and the solubilizer is incorporated into a hydrophilic gel matrix, which gives a prolonged and controlled release of the drug.

The solubilizers suitable for the controlled-release of dihydropyridines according to the invention are nonionic surface-active agents, especially such containing polyethyleneglycols as esters or ethers. They are preferably chosen from polyethoxylated fatty acids, hydroxylated fatty acids and fatty alcohols. It is especially preferred to choose the solubilizer from the group polyethoxylated castor oil, polyethoxylated hydrogenated castor oil, polyethoxylated fatty acid from castor oil or polyethoxylated fatty acid from hydrogenated castor oil. Particularly preferred solubilizers are esters of hydrogenated castor oil fatty acids with oxyethylated glycerine, e.g. polyoxyl 40 hydrogenated castor oil. Commercially available solubilizers, which can be used are known under trade names Cremophor, Myrj, Polyoxyl 40 stearate, Emerest 2675 and Lipal 395.

In the preparation according to the invention the proportion between the solubilizer and the dihydropyridine will be 10:1 or lower, preferably 6:1 or lower.

The β-adrenoreceptor blocking agent is incorporated into the gel system described above in the form of coated beads of active component having a controlled release of the β-adrenoreceptor blocking agent metoprolol during at least 15 hours. This is achieved by preparing a large number of small, preferably compact, particles all comprising a salt of metoprolol as the main soluble component and coated with a water insoluble polymeric membrane. The preferred coating contains non protolysable derivatives of cellulose groups as the main constituent.

The small particles, beads, containing metoprolol have a size of 0.25-2 mm, preferably 0.35–1.0 mm. The beads may consist of the metropolol salt alone or mixed with insoluble excipients or insoluble cores coated with the metoprolol salt.

Metoprolol in the preparation is in the form of the racemate or one of the enantiomers, preferably the S-isomer. Suitable soluble salts of metoprolol have a solubility of less than 600 mg/ml in water at 25° C., preferably 30–600 mg/ml in water at 25° C. Examples of suitable salts are salts formed of organic carboxylic acids, preferably of low molecular weight. Especially preferred are the succinate, fumarate or bensoate of racemic metoprolol and the bensoate or sorbate of the S-enantiomer of metoprolol.

Examples of suitable polymeric materials for coating of the beads are soluble or insoluble derivatives of cell without protolysable groups or acrylic resins like Eudragit RL ®, Eudragit RS ®, alone or in combination. Especially preferred are ethylcellulose in combination with hydroxypropyl methylcellulose or hydroxypropyl cellulose.

The coated beads containing metoprolol described above and which according to the present invention are incorporated into the gel system containing a dihydropyridine are earlier described in No. EP-A-220143. In No. EP-A-220143 it is also described that said beads are a suitable way of preparing a long-acting preparation of metoprolol.

The final preparation is preferably in the form of a tablet, which in the gel-forming matrix contains both the dihydropyridine as well as the metoprolol beads. The metoprolol beads constitute 10-60 weight-%, and the gel forming agents constitute 20-80 weight-% of the preparation. The technical properties of the described controlled release system are excellent, making it very suitable for large scale production. The tablets may optionally be filmcoated to improve appearance and stability.

In vivo, the degree of drug absorption is both high and reproducible. The concentration of drug in plasma and effect over time are governed by the rate of drug release from the system. The release of the dihydropyridine is determined by the properties of the gel forming agents and can be extended over periods up to 24 hours. The rate of release is easily changed to suit a certain dihydropyridine by the use of different types and amounts of gel forming agents of varying properties e.g. viscosity, and gel-strength. The rate of release of metoprolol from the metoprolol beads is modified mainly by the composition and thickness of the polymeric membrane. The release of metoprolol is generally extended over 16-24 hours.

By a careful choice of fillers and binders as well as gel forming material the preparation is manufactured into a commercially acceptable form, e.g. a tablet that shows unexpectedly good absorption of both active compounds as well as a prolonged duration of action.

In the examples below preparations according to the present invention contain 10-20 mg of the dihydropyridine and 95 mg metoprolol succinate. However, depending on the dihydropyridine used and the condition to be treated, the amounts will generally be between 2.5 mg and 80 mg for the dihydropyridine and between 40 and 200 mg for metoprolol racemate as the succinate salt. When the S-enantiomer of metoprolol as the sorbate salt is included the corresponding amounts are between 25 to 120 mg. With other metoprolol salts the amounts will differ in relation to the molecular weight of the salt.

EXAMPLES

Example 1

|  | g |
|---|---|
| Felodipine | 10 |
| Polyoxyl 40 | 25 |

-continued

|  | g |
|---|---|
| hydrogenated castor oil |  |
| Polyvidon K90 | 24 |
| Hydroxypropyl methylcellulose | 230 |
| Aluminum silicate | 94 |
| Lactose | 56 |
| Cellulose, microcrystalline | 6 |
| Metoprolol succinate | 95 |
| SiO$_2$ | 24 |
| Ethylcellulose | 32 |
| Hydroxypropyl methylcellulose | 8 |

The composition according to Example 1 was formed to a tablet containing 10 mg of felodipine and 95 mg metoprolol succinate per tablet. The tablets were prepared in the following way:

I. Felodipine was dissolved in polyoxyl 40 hydrogenated castor oil and the solution obtained was carefully mixed with the carrier materials, HPMC, polyvidone K90, aluminium silicate, lactose and microcrystalline cellulose. The mixture was granulated with ethanol and dried.

II. Metoprolol was sprayed onto cores of silicon dioxide to form beads of 0.5 mm diameter. The beads were coated with a polymeric film by spraying a solution of ethylcellulose and HPMC in methylene chloride and isopropanol onto the beads in a fluidized bed.

I and II were mixed, a lubricant was added and tablets were made by compression in a tablet machine.

The dissolution of both felodipine and metoprolol from the tablet is given in Table 1.

TABLE 1

Cumulative in vitro dissolution of felodipine and metoprolol in a phosphate buffer of pH 6.5 with 1% sodium dodecylsulphate. Method: USP dissolution apparatus No. 2, 50 rpm.

| | Percent released over time (h) | | | | | | |
|---|---|---|---|---|---|---|---|
| | 0 | 2 | 4 | 8 | 12 | 16 | 20 |
| felodipine | 0 | 14 | 32 | 64 | 88 | 96 | 98 |
| metoprolol | 0 | 5 | 16 | 39 | 65 | 86 | 95 |

| Example 2 | g |
|---|---|
| Nifedipine | 20 |
| Myrj 51 | 50 |
| Hydroxypropyl methylcellulose | 200 |
| Xanthan gum | 15 |
| Guar gum | 15 |
| Carboxypolymethylene | 4 |
| Aluminum silicate | 100 |
| Metoprolol succinate | 95 |
| SiO$_2$ | 24 |
| Ethylcellulose | 23 |

The composition according to Example 2 was formed to a tablet containing 20 mg of nifedipine and 95 mg of metoprolol succinate. The tablets were prepared as follows:

I. Nifedipine was dissolved in Myrj 51 and the solution obtained was carefully mixed with the carrier materials, HPMC, xanthan gum, guar gum, carboxypolymethylene and aluminium silicate. The mixture was granulated with ethanol and dried.

II. Metoprolol was sprayed onto cores of silicon dioxide to form beads of 0.5 mm in diameter and coated with a polymeric film of ethylcellulose as described in Example 1.

I and II were mixed, a lubricant was added and tablets made by compression in a tablet machine.

The in vitro dissolution of both nifedipine and metoprolol from the tablet was extended, see Table 2.

TABLE 2

Cumulative in vitro dissolution of nifedipine and metroprolol in a phosphate buffer of pH 6.5 with 1% sodium dodecylsulphate.
Method: USP dissolution apparatus No. 2, 100 rpm.

| | Percent released over time (h) | | | | | |
|---|---|---|---|---|---|---|
| | 0 | 2 | 4 | 8 | 12 | 16 | 20 |
| nifedipine | 0 | 12 | 26 | 44 | 72 | 90 | 98 |
| metoprolol | 0 | 6 | 16 | 34 | 50 | 62 | 75 |

At present both Example 1 and Example 2 are considered to be equally good modes of carrying out the invention.

The following reference examples describe different preparations used in the biopharmaceutical studies. Reference example A illustrates conventional tablets. Reference example B illustrates a preparation, wherein metoprolol has been incorporated into a formulation especially suitable for dihydropyridines and Reference example C illustrates a preparation, wherein felodipine has been incorporated into a controlled release pellet preparation.

Reference example A
Felodipine 10 mg conventional tablets and
Metoprolol 100 mg conventional tablets (100 mg metoprolol tartrate
corresponds to 95 mg metoprolol succinate)
Reference example B

| | g |
|---|---|
| Metoprolol succinate | 95 |
| Polyoxyl 40 hydrogenated castor oil | 25 |
| Hydroxypropyl methylcellulose | 230 |
| Aluminum silicate | 94 |

The composition according to Reference example B was formed to hydrophilic matrix tablets containing 95 mg metoprolol succinate per tablet. The tables were prepared in the following way:

Metroprolol was mixed with polyoxyl 40 hydrogenated castor oil and then carefully mixed with the carrier materials, HPMC and aluminium silicate. The mixture was granulated with ethanol and dried. A lubricant was added and tablets were made by compression in a tablet machine.

The dissolution rate in vitro from this tablet is shown in Table 3.

TABLE 3

Cumulative in vitro dissolution of metoprolol in a phosphate buffer pH 6.8.
Method: USP dissolution apparatus No. 2, 50 rpm.

| Percent released over time (h) | | | | | |
|---|---|---|---|---|---|
| 0 | 1 | 4 | 8 | 12 | 20 |
| 0 | 23 | 59 | 86 | 99 | 100 |

| Reference example C | g |
|---|---|
| Felodipine | 66 |
| Methylcellulose | 13 |
| Mannitol | 870 |
| Polyvinylpyrrolidone | 30 |
| Cellulose, microcrystalline | 40 |
| Ethylcellulose | 34 |
| Polyethyleneglycol | 41.8 |

The composition according to Reference example C was formed to controlled release capsules containing 10 mg of felodipine per capsule. The capsules were prepared in the following way:

Felodipine was micronized and carefully mixed with the carrier, mannitol, methylcellulose, polyvinylpyrrolidone and cellulose. The mixture was moistened with water and spheronized. The granules obtained were dried and sieved, the fraction 0.71–1.12 was used. The fraction was coated with ethylcellulose and polyethylenglycol dissolved in a mixture of methylene chloride and isopropylalcohol. The coated granules were filled into hard gelatine capsules. In vitro, the release of felodipine from the granules was similar to that of the tablet of Example 1.

Biopharmaceutical studies

The extended-release preparation (ER) according to Example 1 was given as a single dose to 12 healthy subjects. In FIG. 1 and 2 the mean plasma curves produced for felodipine and metoprolol as the fixed combination tablet (ER) are shown. The obtained concentration of both drugs in plasma will result in an even effect over 24 hours during continuous therapy.

In FIG. 1 and 2 also the average concentrations of felodipine and metoprolol in plasma after administration of single doses of the conventional tablets, Reference example A, are compared with those after administration of the preparation in Example 1. The metoprolol conventional tablet was given to 10 volunteers and the felodipine conventional tablet to 12 volunteers.

The pellets of Reference example C were given to 6 healthy subjects as a single dose. Plasma samples were taken after 0.5, 1, 2, 3, 4, 6, 8 and 10 hours. In none of the samples could any felodipine be detected.

Discussion

The preparation according to the invention gives a virtually constant and extended release of both felodipine and metoprolol in vitro, Table 1. The corresponding in vivo data shows that the product also gives a controlled and even concentration of both drugs in plasma, FIG. 1 and 2. The advantage of the formulation according to the invention is obvious when comparing the mentioned in vivo data with those after administration of conventional tablets, FIG. 1 and 2. With conventional tablets the concentration of drug plasma is very low 24 hours after administration and in consequence little or no effect may be anticipated. Also the fixed combination of nifedipine and metoprolol in a formulation according to the invention gives the desired extended release of both drugs, cf. Table 2.

As demonstrated by the fast in vitro release of metoprolol from the dosage form of Reference example B, cf. Table 3, it is not possible to achieve the desired release profile over a 20 hour period by just incorporating a metoprolol salt in the hydrophilic swelling matrix used for the dihydropyridine part of the invention. In parallel, it has not been possible to obtain acceptable dihydropyridine plasma levels from a product where the drug without solubilizer is incorporated into coated beads. An in vivo study in healthy subjects of Reference example C gave no detectable levels of felodipine in plasma, cf. above.

To decrease the fluctuation of plasma levels, and to permit once daily dosing of a dihydropyridine derivative and metoprolol an extended release of both drugs is required. This cannot be achieved by use of one single kind of controlled release system according to the prior art. Thus, the present invention which makes use of two separate kinds of controlled release systems incorporated into one unique and new dosage form provides both good absorption and long-effect duration of the two drugs.

We claim:

1. A controlled release preparation for administration once daily and containing a combination of metoprolol and a poorly water soluble a dihydropyridine being a calcium channel blocking agent, wherein metoprolol is included in the form of small beads containing as the main soluble component a salt of metoprolol coated with a waterinsoluble polymeric membrane and the dihydropyridine is dispersed in a non-ionic solubilizer and whereby both the dispersed dihydropyridine and the beads containing metoprolol are incorporated into a matrix forming a swelling gel in contact with water.

2. A preparation according to claim 1 wherein the non-ionic solubilizer is selected from the group polyethoxylated castor oil, polyethoxylated hydrogenated castor oil, polyethoxylated fatty acid from castor oil or polyethoxylated fatty acid from hydrogenated castor oil.

3. A preparation according to claim 1 wherein the non-ionic solubilizer is esters of hydrogenated castor oil fatty acids with oxyethylated glycerine.

4. A preparation according to claim 1 wherein the dihydropyridine is felodipine.

5. A preparation according to claim 1 wherein the dihydropyridine is nifedipine.

6. A preparation according to claim 1 wherein the gel-forming matrix contains hydroxypropyl methylcellulose.

7. A preparation according to claim 1 wherein metoprolol is in the form of its succinate.

8. A preparation according to claim 1 wherein the amount of the dihydropyridine varies between 2.5 mg and 80 mg and the amount of metoprolol succinate racemate between 40 mg and 200 mg.

9. A preparation according to claim 1 wherein metoprolol is in the form of the sorbate of the S-enantiomer and the amount varies between 25 mg and 120 mg.

10. A preparation according to claim 1 wherein metoprolol is in the form of the bensoate or sorbate of the S-enantiomer of metoprolol.

11. A process for the manufacture of a controlled release preparation containing a combination of metoprolol and a poorly water soluble calcium channel blocking agent of the dihydropyridine type characterized in that metoprolol is included in the form of small beads containing as the main soluble component a salt of metoprolol and said beads are spray-coated with a waterinsoluble polymeric membrane, containing derivatives of cellulose without protolysable groups and that said dihydropyridine is dispersed in a non-ionic solubilizer, whereafter both the beads and the dihydropyridine are incorporated into a matrix forming a swelling gel in contact with water.

* * * * *

UNITED STATES PATENT AND TRADEMARK OFFICE
CERTIFICATE OF CORRECTION

PATENT NO. : 4,942,040

DATED : July 17, 1990

INVENTOR(S) : Gert A. Ragnarsson, et al.

It is certified that error appears in the above-identified patent and that said Letters Patent is hereby corrected as shown below:

Col. 1, line 5, "FILED"
Should read --FIELD--;

Col. 1, line 16, "acheiving"
Should read --achieving--;

Col. 1, line 36, "litterature"
Should read --literature--;

Col. 2, line 25, "dissintegration"
Should read --disintegration--;

Col. 3, line 27, "means"
Should read --mean--;

UNITED STATES PATENT AND TRADEMARK OFFICE
CERTIFICATE OF CORRECTION

PATENT NO. : 4,942,040

DATED : July 17, 1990

INVENTOR(S) : Gert A. Ragnarsson, et al.

It is certified that error appears in the above-identified patent and that said Letters Patent is hereby corrected as shown below:

```
Col. 5, line 27, "cell"
Should read --cellulose--;

Col. 6, line 65, "and II"
Should read --I and II--;

Col. 7, line 40, "tables"
Should read --tablets--;
```

Signed and Sealed this

Twelfth Day of May, 1992

Attest:

DOUGLAS B. COMER

*Attesting Officer*     *Acting Commissioner of Patents and Trademarks*